(12) United States Patent
Göbbel et al.

(10) Patent No.: US 7,005,554 B2
(45) Date of Patent: Feb. 28, 2006

(54) METHOD FOR CONTINUOUS HYDROGENATION OF CITRONELLAL TO FORM CITRONELLOL

(75) Inventors: Hans-Georg Göbbel, Kallstadt (DE); Till Gerlach, Ludwigshafen (DE); Günter Wegner, Roemerberg (DE); Hartwig Fuchs, Ludwigshafen (DE); Signe Unverricht, Mannheim (DE); Axel Salden, Stuttgart (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/519,686

(22) PCT Filed: Jul. 14, 2003

(86) PCT No.: PCT/EP03/07599

§ 371 (c)(1),
(2), (4) Date: Jan. 10, 2005

(87) PCT Pub. No.: WO2004/007411

PCT Pub. Date: Jan. 22, 2004

(65) Prior Publication Data

US 2005/0256347 A1    Nov. 17, 2005

(30) Foreign Application Priority Data

Jul. 15, 2002  (DE)  ................ 102 31 942

(51) Int. Cl.
*C07C 29/141*  (2006.01)
(52) U.S. Cl. .................. 568/881; 568/875
(58) Field of Classification Search ............. 568/881, 568/875
See application file for complete search history.

(56) References Cited

U.S. PATENT DOCUMENTS

| | | |
|---|---|---|
| 3,346,650 A | 10/1967 | Kane |
| 4,029,709 A | 6/1977 | De Simone et al. |
| 5,939,589 A | 8/1999 | Kaibel et al. |

FOREIGN PATENT DOCUMENTS

EP   1 318 129   6/2003

*Primary Examiner*—Elvis O. Price
(74) *Attorney, Agent, or Firm*—Oblon, Spivak, McClelland, Maier & Neustadt, P.C.

(57) ABSTRACT

A process is described for selectively hydrogenating citronellal to citronellol in which a liquid phase, in which the citronellal is dissolved and particles of a catalyst are suspended which is capable of preferentially hydrogenating carbon-oxygen double bonds over carbon—carbon double bonds, is conducted through a device which inhibits the transport of the catalyst particles in the presence of a hydrogen-containing gas.

8 Claims, 2 Drawing Sheets

METHOD FOR CONTINUOUS HYDROGENATION OF CITRONELLAL TO FORM CITRONELLOL

Figure 1:
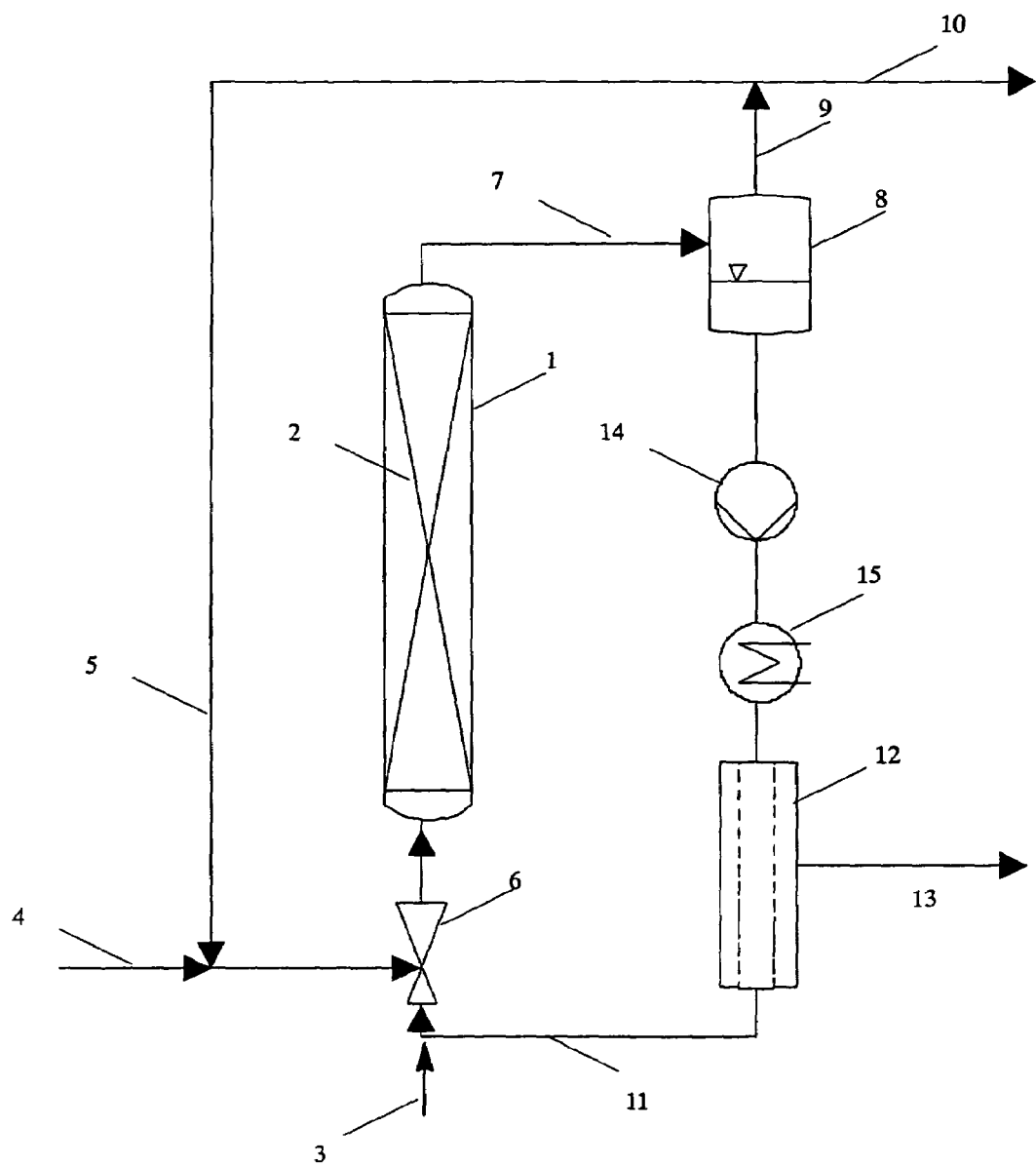

The present invention relates to a process for continuously and selectively hydrogenating citronellal to citronellol (Scheme 1).

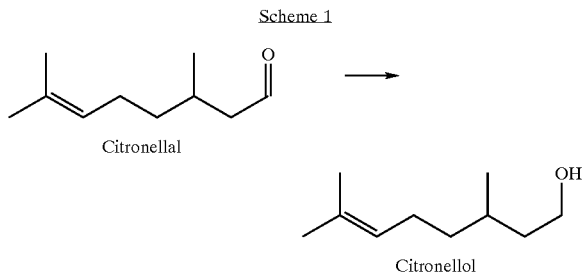

Scheme 1

Citronellal

Citronellol

Citronellol finds use as a scent and aroma.

U.S. Pat. No. 3,346,650 discloses a process for preparing citronellol by hydrogenating a mixture of geraniol and nerol over a copper chromate catalyst.

Catalytic hydrogenations over heterogeneous catalysts are in many cases carried out using fixed bed reactors in order to obtain the advantages of continuous process operation. However, specially prepared catalysts have to be produced and used, and when they lose activity, often after only short onstream times, have to be exchanged or regenerated in a costly and inconvenient manner which generally involves not only the shutdown of the hydrogenation plant, but also the subsequent workup stages.

Alternatively, a heterogeneously catalyzed hydrogenation may be carried out in the form of a suspension reaction by suspending the hydrogenation catalyst in a liquid phase through the introduction of mechanical energy, for example in a stirred tank, c.f., for example, Ullmanns Encyklopädie der technischen Chemie, 4th Ed., Volume 13, 1997, p. 138, Verlag Chemie Weinheim. An increase in the energy introduced over and above the contribution necessary for suspension does not lead to a significant improvement in the mass transfer of the molecules to be hydrogenated to the surface of the catalyst particles, since the achievable relative velocity between the catalyst particles and the liquid phase only slightly exceeds the sedimentation velocity. Although flow or fluidized bed reactors allow higher relative velocities, they require the use of distinctly larger catalyst particles so that a catalyst bed is more or less extensively expanded in the course of operation. However, the lower surface area relative to volume of large catalyst particles lowers the material conversion and thus compensates for the effect of higher relative velocity.

EP-A 798 039 discloses a process for carrying out catalytic reactions in a reactor which contains a liquid phase in which at least one catalyst is suspended. The hydrogenation of hydrodehydrolinalool to hydrolinalool and further to tetrahydrolinalool is described. Hydrodehydrolinalool contains only one triple bond as a functional group to be hydrogenated, so those skilled in the art would not have discerned any suggestion with regard to selective hydrogenation.

It is an object of the present invention to provide a process for selectively hydrogenating citronellal to citronellol which combines the advantages of high space-time yield and simple catalyst exchange.

We have found that this object is achieved by a process in which a liquid phase, in which the citronellal is dissolved and particles of a catalyst are suspended which is capable of preferentially hydrogenating carbon-oxygen double bonds over carbon—carbon double bonds, is conducted through a device which inhibits the transport of the catalyst particles in the presence of a hydrogen-containing gas.

In the process according to the invention, a relatively high relative velocity of liquid phase compared to the catalyst particles is obtained because the transport of the catalyst particles is inhibited by suitable means such as internals in a reactor, i.e. the particles are more strongly held back than the surrounding liquid. In combination with the high surface area relative to volume on the suspended particles, high space-time yields are achieved as a result.

A suitable apparatus for carrying out the process according to the invention is described in EP-A 798 039.

The device inhibiting the transport of the catalyst particles preferably has orifices or channels whose hydraulic diameter is from 2 to 2000 times, in particular from 5 to 500 times, more preferably from 5 to 100 times, the average diameter of the catalyst particles.

The hydraulic diameter is a measure familiar to those skilled in the art for describing the equivalent diameter of noncircular channel structures. The hydraulic diameter of an orifice is defined as the quotient of 4 times the cross-sectional area of the orifice and its circumference. In the case of channels having a cross section in the shape of an isosceles triangle, the hydraulic diameter can be described as $$\frac{2bh}{b+2s}$$

where b is the base, h is the height and s is the congruent length of the triangle.

The orifices or channels of suitable devices generally have a hydraulic diameter of from 0.5 to 20 mm, preferably from 1 to 10 mm, more preferably from 1 to 3 mm.

Customarily, catalyst particles are used which have an average diameter of from 0.0001 to 2 mm, preferably from 0.001 to 1 mm, more preferably from 0.005 to 0.1 mm.

The device inhibiting the transport of the catalyst particles may comprise a dumped packing, a knit, an open-celled foam structure, preferably made of plastic, for example polyurethane or melamine resin, or ceramic, or a structured packing element, as already known in principle, i.e. by its geometric shape, from distillation and extraction technology. However, for the purposes of the present invention, the structured packings in principle have a substantially smaller hydraulic diameter, frequently by a factor of from 2 to 10, than comparable internals in the field of distillation and extraction technology.

Useful structured packing elements are in particular metal fabric packings and wire fabric packings, for example of the design Montz A3, Sulzer BX, DX and EX. Instead of metal fabric packings, it is also possible to use structured packings made of other woven, knitted or felted materials. Further useful structured packings are of flat or corrugated sheet, preferably without perforation or other relatively large orifices, for example corresponding to the designs Montz B1 or Sulzer Mellapak. The structured packings made of expanded metal are also advantageous, for example packings of a type Montz BSH. A decisive factor for the suitability of a structured packing for the purposes of the present invention is not its geometry, but rather the orifice sizes and channel widths available for liquid flow.

In a preferred embodiment, the surfaces of the device facing toward the liquid phase have a roughness in the region of from 0.1 to 10 times, preferably from 0.5 to 5 times, the average diameter of the catalyst particles. Preference is given to materials whose surfaces have an average roughness value $R_a$ (determined according to DIN 4768/1) of from 0.001 to 0.01 mm. When woven stainless steel wire packings are used, an appropriate surface roughness may be achieved by thermal treatment in the presence of oxygen, for example by heat treating the weave under air at a temperature of about 800° C.

The process according to the invention is generally effected at a pressure of from 1 to 100 bar, preferably from 1 to 60 bar, more preferably from 1 to 50 bar. The reaction temperatures are customarily from 40 to 120° C., preferably from 60 to 100° C., more preferably from 70 to 90° C.

In addition to citronellal, the liquid phase preferably comprises an inert diluent, in particular a $C_1$–$C_6$-alkanol, more preferably a $C_1$–$C_4$-alkanol, in particular methanol. The liquid phase preferably further comprises ammonia, a primary, secondary and/or tertiary amine, of which preference is given to tertiary amines, for example tri($C_1$–$C_4$-alkyl)amines, in particular trimethylamine. The concentration of citronellal in the liquid phase is preferably from 50 to 90% by weight, more preferably from 60 to 80% by weight, that of the diluent is from 40 to 50% by weight, preferably from 20 to 35% by weight, and that of the ammonia/amine is from 1 to 15% by weight, preferably from 1 to 8% by weight.

The hydrogen-containing gas used is generally hydrogen gas having a purity of at least 99.5% by volume. It is used in at least a stoichiometric amount based on the carbonyl compound present in the liquid phase, usually in an excess of from 1 to 20%.

The catalyst used may be a commercial suspension catalyst which is capable of preferentially hydrogenating carbon-oxygen double bonds over carbon—carbon double bonds. Particularly useful catalysts are those which comprise at least ruthenium as the active component. In addition to ruthenium, the catalyst may also comprise further active components, for example iron. The catalyst may be used in metallic and/or oxidic form. Preference is given to applying the active components to a support material. Examples of useful support materials include $SiO_2$, $TiO_2$, $ZrO_2$, $Al_2O_3$ or carbon such as graphite, carbon blacks or activated carbon. Preference is given to activated carbon owing to its easy suspendability. The content of ruthenium is preferably 0.1 to 10% by weight, the content of iron is preferably 0.1 to 5% by weight, in particular 0.5 to 1.5% by weight, based on the total weight of the catalyst.

The suspended catalyst material may be introduced into the liquid phase and is distributed within it with the aid of conventional techniques.

The device inhibiting the transport of the catalyst particles is customarily a plurality of internals in a reactor which are configured in such a manner that the reaction mixture is forced through the device when it passes through the reactor, i.e. the internals generally fill the entire free cross section of the reactor. The internals preferably, but not necessarily, extend over the entire elongation of the reactor in the flow direction of the liquid phase.

Various reactor forms are suitable, such as jet nozzle reactors, bubble columns or tube bundle reactors. Among these, particularly suitable reactors are vertical bubble columns or tube bundle reactors in which the internals are accommodated in the individual tubes.

Preference is given to conducting the hydrogen-containing gas and the liquid phase in cocurrent through the reactor, preferably against the direction of gravity. The gas phase is intimately mixed with the liquid phase, for example, by means of an injector nozzle. The superficial velocity of the liquid phase is preferably more than 100 m³/m²h, in particular from 100 to 250 m³/m²h, and that of the gas phase is preferably more than 100 Nm³/m²h (STP), in particular from 100 to 250 Nm³/m²h (STP). In order to achieve sufficiently high superficial velocities, preference is given to recycling substreams of the gas and liquid phases which leave the reactor.

The catalyst particles suspended in the hydrogenation effluent are removed by customary processes, for example by sedimentation, centrifugation, cake filtration or crossflow filtration.

The hydrogenation of the invention may be either continuous or batchwise, but preferably proceeds continuously.

The process according to the invention is illustrated by the appended figure and the example which follows.

FIG. 1 shows a schematic of a plant suitable for carrying out the process according to the invention comprising a reactor (bubble column) 1 having a structured packing 2 which inhibits the transport of the catalyst particles. Liquid is introduced into the reactor 1 via the lines 3 and hydrogen gas via the line 4. The cycle gas 5 is mixed with fresh gas using the mixing nozzle 6 and the suspension 11 circulated by the pump 14. The reactor effluent is transferred via the line 7 into the separating vessel 8 in which the gas phase is separated and removed via line 9. A substream of this gas is withdrawn via the line 10 to limit the accumulation of gaseous impurities and the residue is conducted into the reactor via the line 5. The suspended catalyst remains in the reactor system by being held back by a crossflow filter 12 and only catalyst-free liquid phase exits via the line 13 and is withdrawn. The heat exchanger 15 can be used to precisely adjust the temperature in the reactor system.

Figure 2:
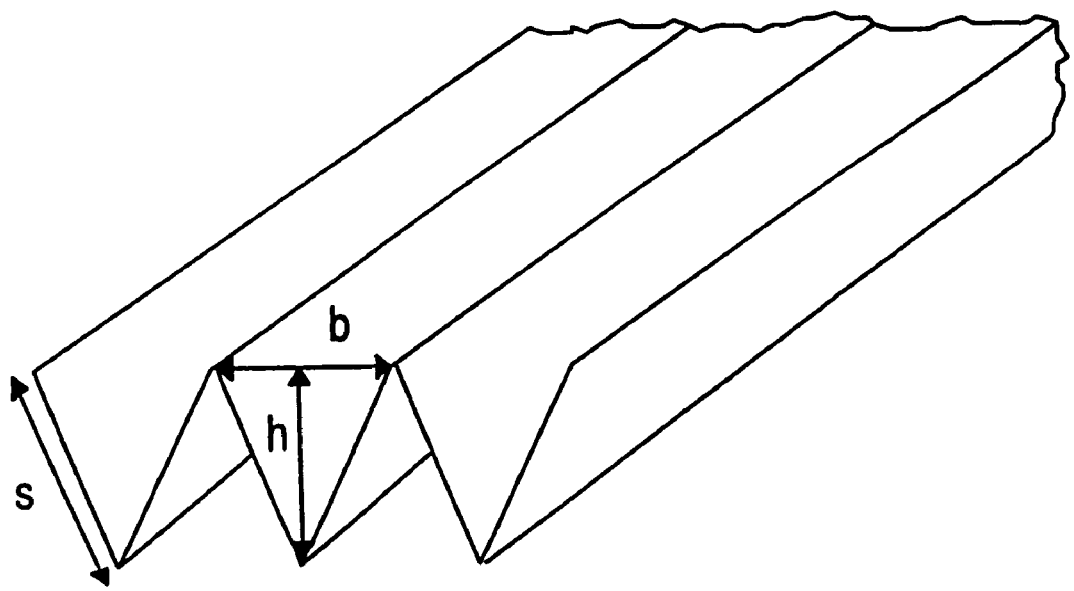

FIG. 2 shows a schematic of a layer of a corrugated weave. Structured packings usable according to the invention are obtained when two or more of these layers are arranged on top of one another. Each layer comprises channels having a cross section in the shape of an isosceles triangle having the congruent length s, the base b and the height h.

EXAMPLE 1

A plant as described in FIG. 1 was used which comprised a bubble column (3000 mm length, 27.3 mm diameter) equipped with a structured woven packing of the type Montz A1 1200. The structured packing consisted of layers arranged on top of one another of a stainless steel wire weave which was corrugated in such a manner that channels having a cross section in the shape of an isosceles triangle were formed of which the congruent length was 3.1 mm, the base 5.1 mm and the height 1.8 mm, corresponding to a hydraulic diameter of 1.62 mm.

The feed used was a mixture of 70% by weight of citronellal, 27% by weight of methanol and 3% by weight of trimethylamine. A Ru/Fe-carbon suspension catalyst which comprised 5% of ruthenium and 1% of iron on activated carbon and had an average particle size of about 50 μm was suspended in the feed. The reaction was continuous under a hydrogen pressure of 20 bar and a temperature of 80° C. The liquid comprising the suspended catalyst and the gas was introduced from below into the packed reactor at a superficial velocity of 200 m³/m²h.

The conversion was more than 95% at a selectivity of 9% for citronellol. The catalyst hourly space velocity was 40.2 $kg_{citronellal}/kg_{Rh} \cdot h$, and the space-time yield 233 $kg_{citronelol}/m^3 \cdot h$.

We claim:

1. A process for selectively hydrogenating citronellal to citronellol, comprising conducting a liquid phase, in which the citronellal is dissolved and particles of a catalyst are suspended, which is capable of preferentially hydrogenating carbon-oxygen double bonds over carbon—carbon double bonds, through a device which inhibits the transport of the catalyst particles in the presence of a hydrogen-containing gas, and wherein the liquid phase further comprises ammonia, a primary, secondary and/or tertiary amine, as well as an inert diluent, and wherein the concentration of citronellal in the liquid phase is from 50 to 90% by weight.

2. The process as claimed in claim 1, wherein the active component of the catalyst comprises ruthenium.

3. The process as claimed in claim 1, wherein the device inhibiting the transport of the catalyst particles has orifices or channels whose hydraulic diameter is from 2 to 2000 times the average diameter of the catalyst particles.

4. The process as claimed in claim 1, wherein catalyst particles having an average diameter of from 0.0001 to 2 mm are used.

5. The process as claimed in claim 1, wherein the device inhibiting the transport of the catalyst particles is a dumped packing, a knit, an open-celled foam structure or a structured packing element.

6. The process as claimed in claim 1, wherein the liquid phase and the hydrogen-containing gas are conducted through the device inhibiting the transport of the catalyst particles, at a superficial velocity of more than 100 m³/m²h.

7. The process as claimed in claim 1, wherein the surfaces of the device, facing toward the liquid phase, have a roughness in the region of from 0.1 to 10 times the average diameter of the catalyst particles.

8. The process as claimed in claim 1, wherein the diluent is a $C_1$–$C_6$-alkanol.

* * * * *